US006962758B2

(12) United States Patent
Chen et al.

(10) Patent No.: US 6,962,758 B2
(45) Date of Patent: Nov. 8, 2005

(54) ORGANIC LIGHT-EMITTING DEVICE USING IPTYCENE DERIVATIVES

(75) Inventors: Jian Ping Chen, San Jose, CA (US); Yoshimasa Okamura, Sunnyvale, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/883,802

(22) Filed: Jul. 6, 2004

(65) Prior Publication Data

US 2004/0253479 A1 Dec. 16, 2004

Related U.S. Application Data

(62) Division of application No. 10/230,273, filed on Aug. 29, 2002, now abandoned.

(51) Int. Cl.$^7$ .............................................. H05B 33/14
(52) U.S. Cl. ........................ 428/690; 428/917; 428/704; 313/504; 313/506; 252/301.35; 257/40; 257/103; 556/64; 556/406
(58) Field of Search ................................. 428/690, 917, 428/704; 313/504, 506; 252/301.35; 257/40, 103; 556/64, 406

(56) References Cited

U.S. PATENT DOCUMENTS

| | | | |
|---|---|---|---|
| 4,371,690 A | 2/1983 | Anderson et al. | 528/190 |
| 4,435,548 A | 3/1984 | Tomalia et al. | 525/451 |
| 4,507,466 A | 3/1985 | Tomalia et al. | 528/332 |
| 4,558,120 A | 12/1985 | Tomalia et al. | 528/363 |
| 4,626,361 A | 12/1986 | Molaire | 252/1 |
| 4,631,337 A | 12/1986 | Tomalia et al. | 528/391 |
| 4,883,898 A | 11/1989 | Yang | 558/427 |
| 4,946,890 A | 8/1990 | Meador | 524/600 |
| 5,041,516 A | 8/1991 | Frechet et al. | 528/44 |
| 6,025,462 A | 2/2000 | Wang et al. | 528/377 |
| 6,268,072 B1 | 7/2001 | Zheng et al. | 428/690 |
| 6,294,245 B1 | 9/2001 | Roitman et al. | 428/212 |
| 6,361,886 B2 | 3/2002 | Shi et al. | 428/690 |
| 6,509,110 B1 | 1/2003 | Salbeck et al. | 428/690 |
| 6,649,283 B1 * | 11/2003 | Lupo et al. | 428/690 |
| 2002/0011420 A1 | 1/2002 | Roitman et al. | 205/419 |
| 2002/0040805 A1 | 4/2002 | Swager | 174/110 |
| 2002/0150697 A1 | 10/2002 | Swager et al. | 428/1.1 |
| 2003/0178607 A1 | 9/2003 | Swager et al. | 252/582 |

FOREIGN PATENT DOCUMENTS

| | | | | |
|---|---|---|---|---|
| EP | WO-0036660 | * | 7/2000 | ........... H05B/33/14 |
| EP | 1 281 744 | | 2/2003 | |
| WO | 99/57222 | | 11/1999 | |
| WO | 02/16463 | | 2/2002 | |

OTHER PUBLICATIONS

K. Shahlai, et al., "Synthesis of Three helically Chiral Iptycenes", J. Org. Chem., vol. 56, pp. 6912–6916 (1991).
K. Shahlai, et al., "Synthesis of Supertriptycene and Two Related Iptycenes", J. Org. Chem., vol. 56, pp. 6905–6912 (1991).
K. Shahlai, et al., "A Method for the Synthesis of Angular Iptycenes", J. Org. Chem., vol. 54, pp. 2615–2620 (1989).
H. Hart, et al., "Iptycenes", Tetrahedron, vol. 42, No. 6, pp. 1641–1654 (1986).
N. Maigrot, et al., "New and Improved Synthesis of Optically Pure (R) and (S)–2,2'–Dimethyl–1,1'–binaphthyl and Related Compounds", Synthesis, vol. 3, pp. 317–320 (1985).
J. Yang, et al., "Porous Shape Persistant Fluorescent Polymer Films: An Approach to TNT Sensory Materials", J. Am. Chem. Soc., vol. 120, pp. 5321–5322 (1998).
J. Yang, et al., "Fluorescent Porous Polymer Films as TNT Chemosensors: Electronic and Structural Effects", J. Am. Chem. Soc., vol. 120, pp. 11864–11873 (1998).
A. Hashemi, et al., "Tritriptycene: A $D_{3h}C_{62}$ Hydrocarbon with Three U–Shaped Cavities", J. Am. Chem. Soc., vol. 108, pp. 6675–6679 (1986).
V.E. Williams, et al., "Iptycene–Containing Poly(arylene-ethynylene)s", Macromolecules, vol. 33, pp. 4069–4073 (2000).
J. Yang, et al., "Conformation and Monolayer Assembly Structure of a Pentiptycene–Derived α,ω–Alkanedithiol", J. Org. Chem., vol. 65, pp. 871–877 (2000).
J. Yang, et al., "Anomalous Crystal Packing of Iptycene Secondary Diamides Leading to Novel Chain and Channel Networks", Tetrahedron Lett., vol. 41, pp. 7911–7915 (2000).
X. Li, et al., "Synthesis, Properties, and Application of New Luminescent Polymers with Both Hole and Electron Injection Abilities for Light–Emitting Devices", Chem. Mater., vol. 11, pp. 1568–1575 (1999).
T.M. Long, et al., "Minimization of Free Volume: Alignment of Triptycenes in Liquid Crystals and Stretched Polymers", Adv. Mater., vol. 13, No. 8, pp. 601–604 (2001).
J. Tian, et al., "Electroluminescent Properties of Self–Assembled Polymer Thin Films", Adv. Mater., vol. 7, No. 4, pp. 395–398 (1995).
D.D. Gebler, et al., "Blue Electroluminescent Devices Based on Soluble Poly(p–pyridine)", J. Appl. Phys., vol. 78, No. 6, pp. 4264–4266 (1995).

* cited by examiner

*Primary Examiner*—Deborah Jones
*Assistant Examiner*—Ling Xu
(74) *Attorney, Agent, or Firm*—Fitzpatrick, Cella, Harper & Scinto

(57) ABSTRACT

An organic light-emitting device (OLED) in which an iptycene derivative is used as the emissive layer and/or one or more of the charge transport layers, or as a host material for one or more of these layers.

3 Claims, No Drawings

ORGANIC LIGHT-EMITTING DEVICE USING IPTYCENE DERIVATIVES

This application is a division of Application Ser. No. 10/230,273 filed Aug. 29, 2002, now abandoned the entire disclosure of which is incorporated herein by reference.

BACKGROUND OF THE INVENTION

1. Field of the Invention

The present invention relates to an organic light emitting device (OLED) in which small molecule iptycene derivatives are used as the emissive layer and/or one or more of the charge transport layers, or as a host material for one or more of such layers.

2. Description of the Related Art

Significant efforts have been expended in developing suitable materials for use in organic light emitting devices (OLEDs). Such devices are commercially attractive because they offer the promise of low-cost fabrication of high-density pixeled displays exhibiting bright electroluminescence with long life times and wide color range.

A typical OLED is fabricated by sandwiching an emissive layer between an anode and a cathode. When a bias is applied across the electrodes, holes and electrons are respectively injected from the anode and cathode into the emissive layer, typically facilitated by hole transport and electron transport layers (charge transport layers) adjacent to the respective electrodes. The holes and electrons radiatively combine in the emissive layer and emit light. Improved performance can be obtained if blocking layers are provided to block against the injection of either holes or electrons from the adjoining layer and their subsequent escape from the device. Some of these layers can be combined. For example, a double-layered structure is fabricated from a combined hole-injecting and transporting layer together with a combined electron-transporting and light-emitting layer. Likewise, a triple-layered structure is composed of a hole-injecting and transporting layer, a light-emitting layer, and an electron-injecting and transporting layer.

In addition, it is possible to form these layers from a host material doped with another material designed to achieve the desired effect of the layer (for example, to achieve a hole transport effect, an electron transport effect, or an emissive effect).

Because of consumer expectations of good efficiency, long lifetime and pure color, a need exists for development of suitable materials for the various layers.

SUMMARY OF THE INVENTION

It is an object of the invention to provide an improved OLED in which iptycene derivatives are used as the emissive layer and/or one or more of the charge transport layers, or as a host material for one or more of such layers.

Thus, in one aspect, the invention is an OLED in which an emissive layer is sandwiched between at least a cathode and an anode, and in which the emissive layer includes an iptycene derivative expressed according to the following general formula (I):

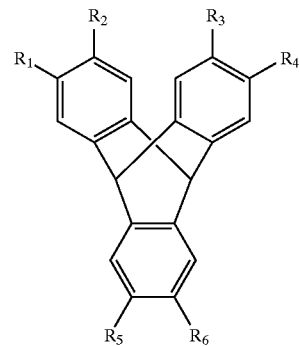

(I)

wherein any or all of $R_1$–$R_6$ may be absent; wherein any or all of $R_1$ and $R_2$, $R_3$ and $R_4$, and $R_5$ and $R_6$ may be taken together to form an aryl group; and wherein any or all of $R_1$–$R_6$ may represent a charge-transport substituent.

The compound expressed according to formula (I) can be used directly as the emissive layer, or can be used as a host material for an emissive dopant in a case where the emissive layer comprises an iptycene host plus an emissive dopant.

In a further aspect, the invention is an OLED having an emissive layer sandwiched between at least one charge transport layer and an anode and a cathode. The charge transport layer can be either an electron transport layer or a hole transport layer, or both. According to this aspect of the invention, the charge transport layer includes an iptycene derivative according to the above general formula (I) wherein $R_1$ through $R_6$ are specified above.

According to this aspect, the compound expressed according to formula (I) can be used directly as the charge transport layer or can form a charge transport host material in a case where the charge transport layer comprises a host material plus a charge transport dopant.

In certain preferred embodiments of the present invention, any or all of $R_1$ and $R_2$, $R_3$ and $R_4$, and $R_5$ and $R_6$ are taken together to form an aryl group selected from the group consisting of

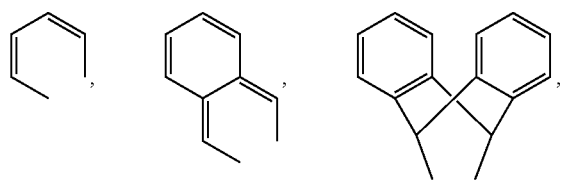

-continued
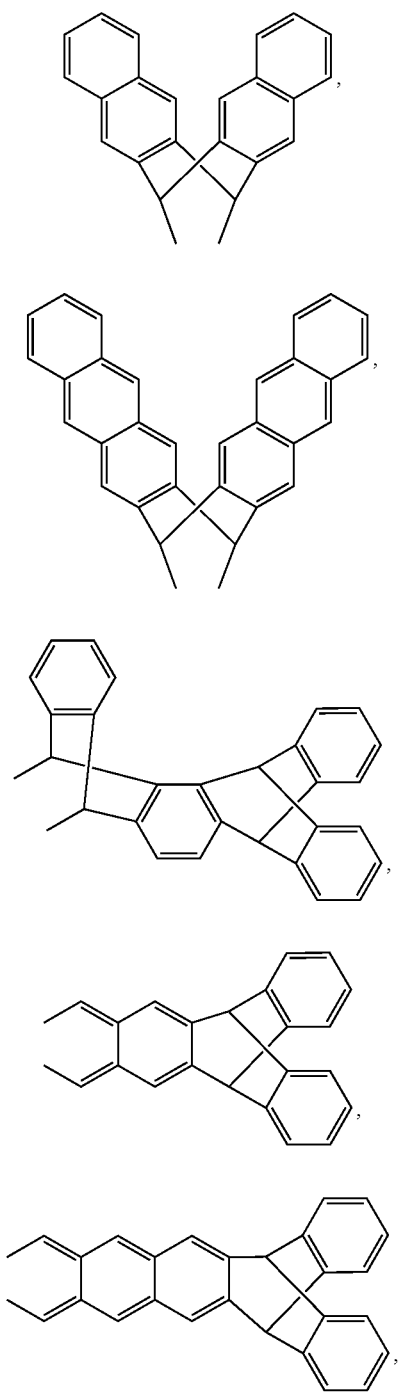
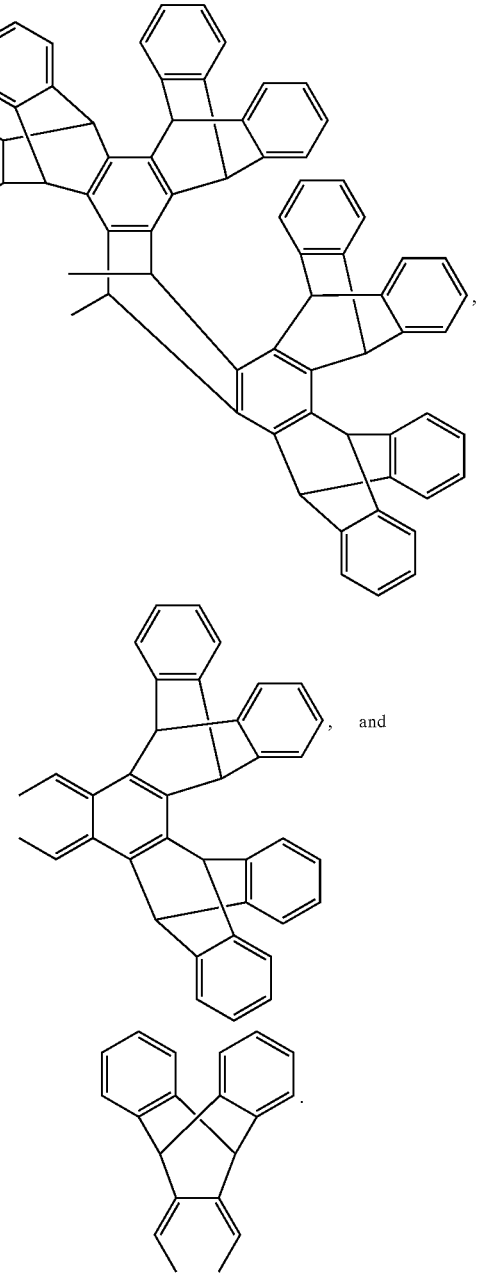
In certain preferred embodiments of the present invention, any or all of $R_1$–$R_6$ represents a charge-transport substituent selected from the group consisting of
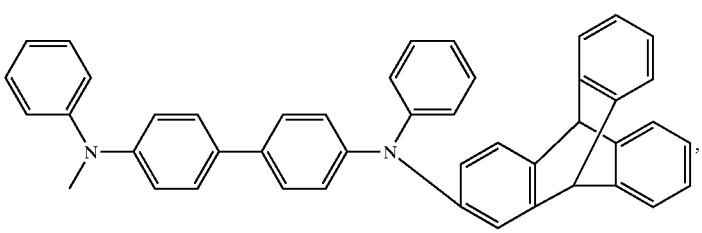

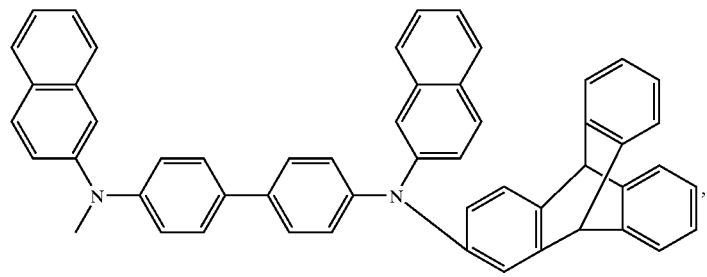
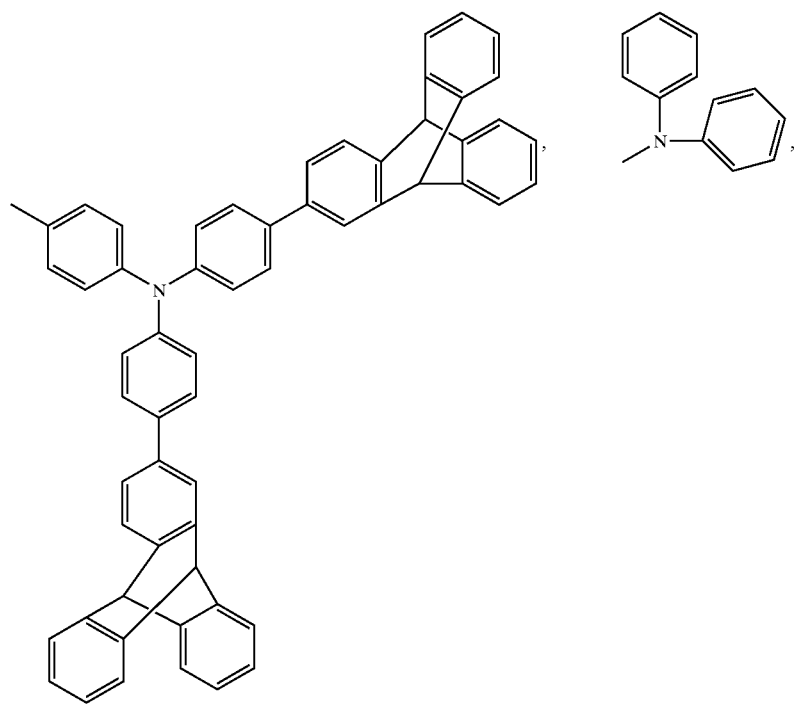
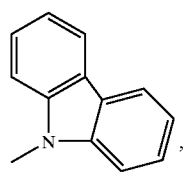
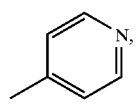

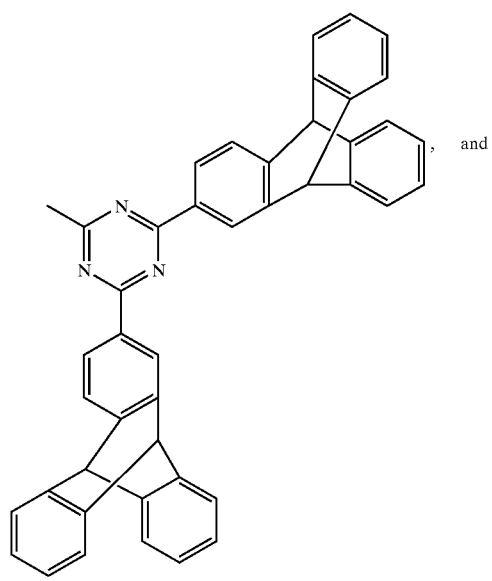
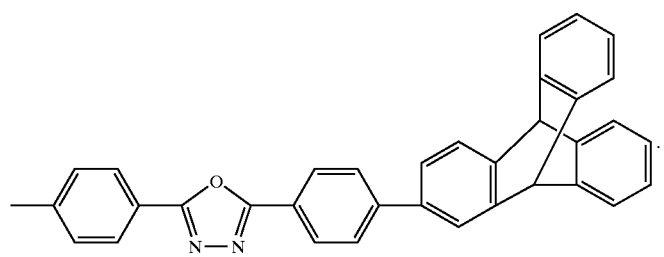
In preferred embodiments of the present invention, the iptycene derivative is selected from the group consisting of
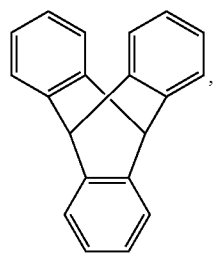
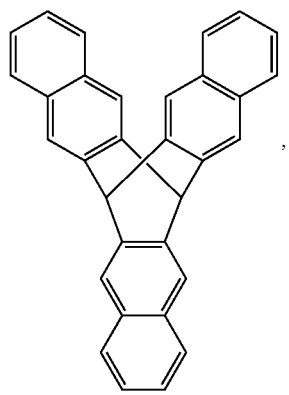

-continued
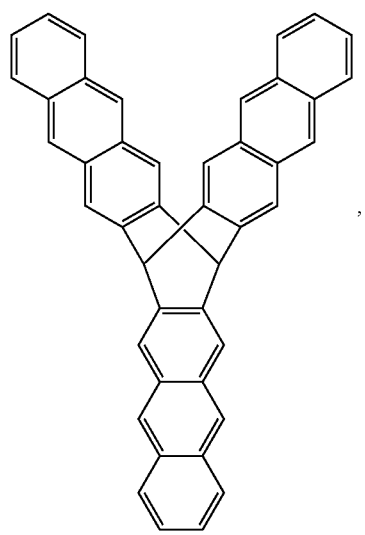
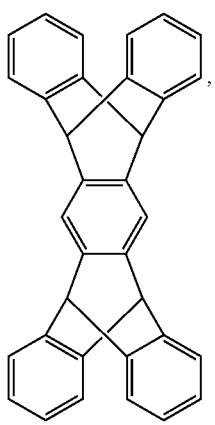
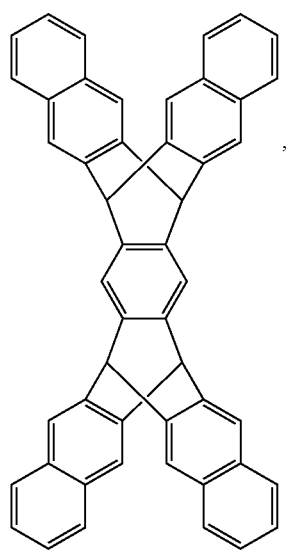
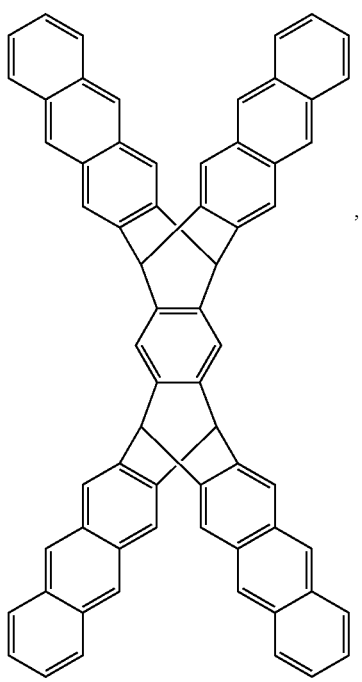
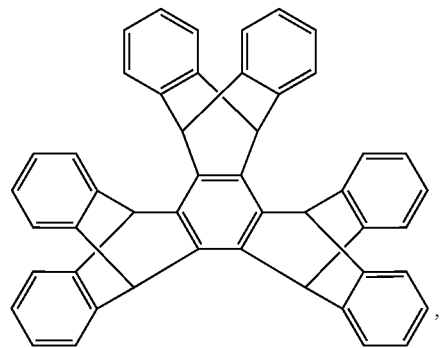
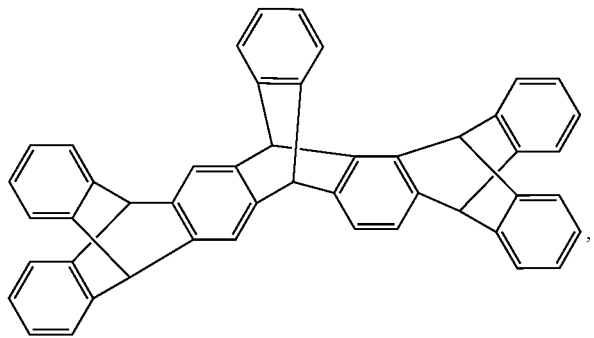

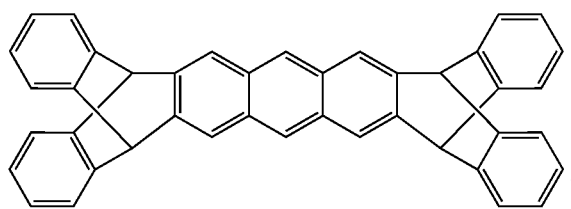
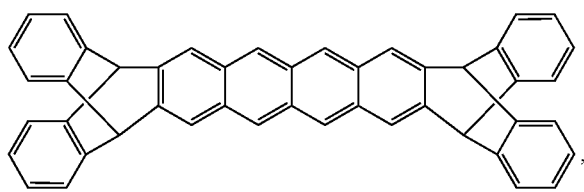
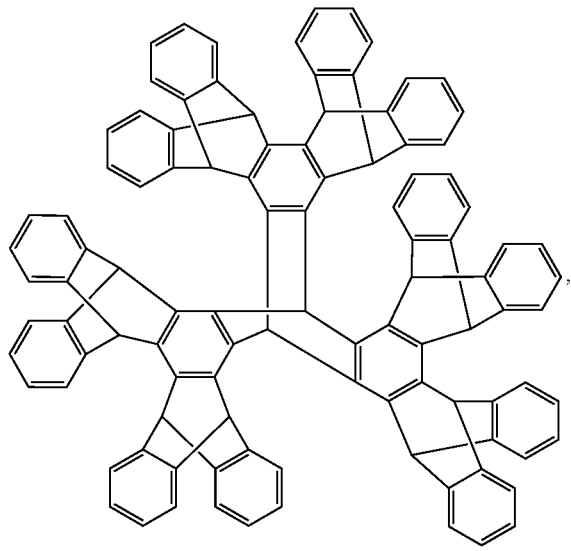
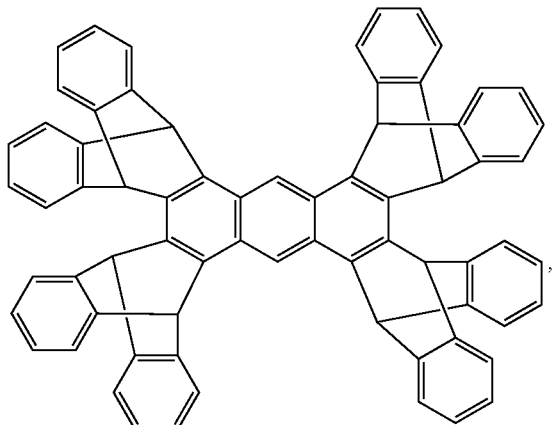
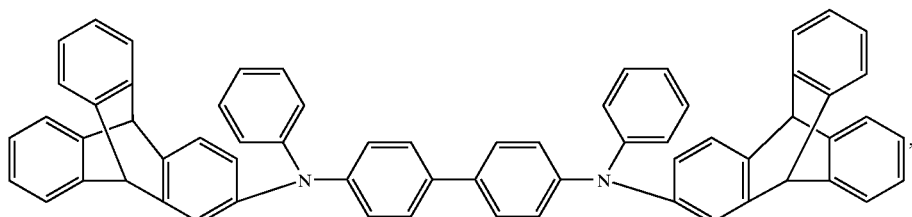
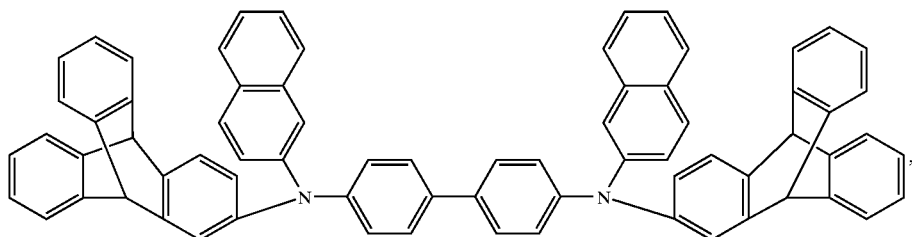
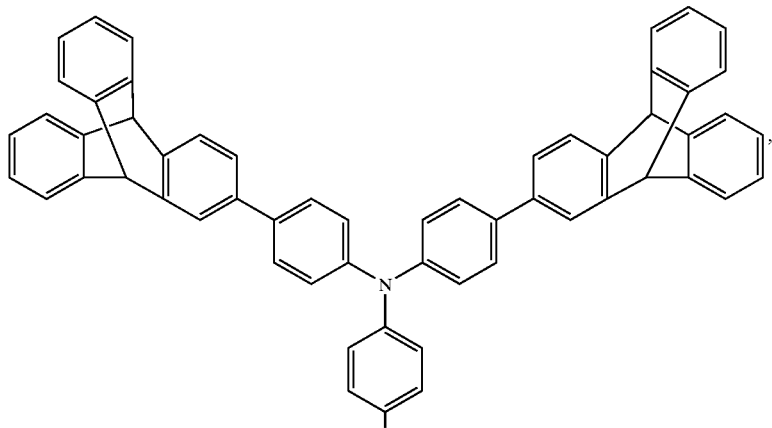

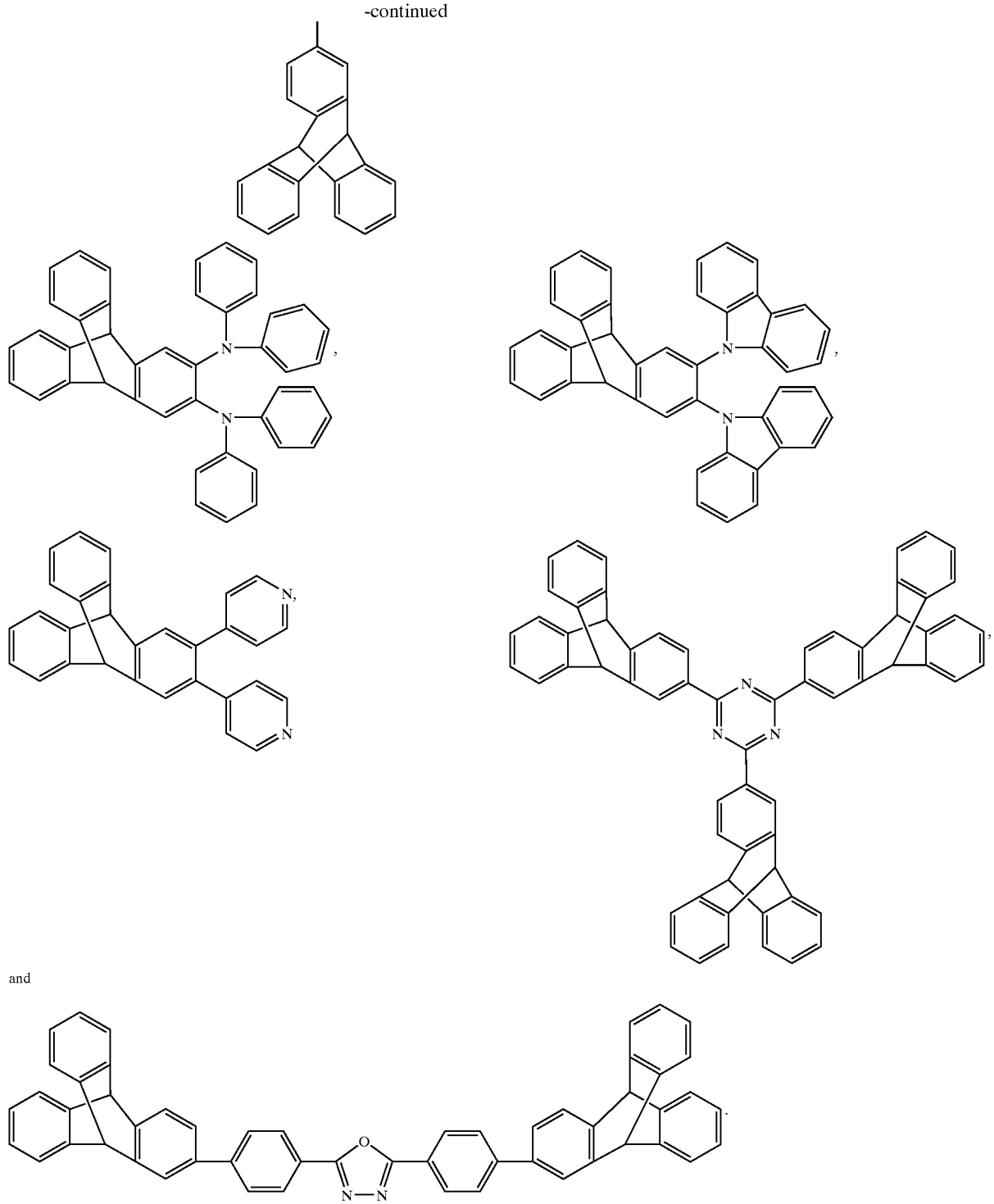

and

This brief summary has been provided so that the nature of the invention may be understood quickly. A more complete understanding of the invention can be obtained by reference to the following detailed description of the preferred embodiment thereof in connection with the attached drawings.

DETAILED DESCRIPTION OF THE PREFERRED EMBODIMENTS

In general, iptycenes have a rigid carbon framework, show exceptional thermal stability, and have well-defined 3-D molecular structures. Therefore, a device layer comprising small molecule iptycenes or small molecule iptycene derivatives, i.e., non-polymeric iptycenes, would prevent close molecular packing. As a result, high photoluminescent efficiency and possibly high electroluminescent efficiency can be achieved.

Iptycene and iptycene derivatives suitable for use in the present invention can be produced according to any known method. Exemplary syntheses are disclosed in Shahlai, et al., "Synthesis of Three Helically Chiral Iptycenes", J. Org.

Chem., vol. 56, no. 24, p. 6912 (1991); Shahlai, et al., "Synthesis of Supertriptycene and Two Related Iptycenes", J. Org. Chem., vol. 56, no. 24, p. 6905 (1991); Shahlai, et al., "A Method for the Synthesis of Angular Iptycenes", J. Org. Chem., vol. 54, no. 11, pp. 2615 (1989); and Hart, et al., "Iptycenes: Extended Triptycenes", Tetrahedron, vol. 42, no. 6, pp. 1641 (1986). In addition, unsubstituted triptycene is commercially available from a source such as Aldrich Chemical.

Accordingly, in one aspect the invention is an OLED in which an emissive layer is sandwiched between at least a cathode and an anode, and in which the emissive layer includes an iptycene derivative expressed according to the following general formula (I):

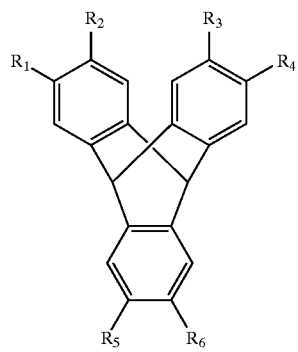

(I)

wherein any or all of $R_1$–$R_6$ may be absent; wherein any or all of $R_1$ and $R_2$, $R_3$ and $R_4$, and $R_5$ and $R_6$ may be taken together to form an aryl group; and wherein any or all of $R_1$–$R_6$ may represent a charge-transport substituent.

Any or all of $R_1$–$R_6$ may be absent. If all of $R_1$–$R_6$ are absent, then the iptycene derivative is unsubstituted triptycene.

When present, any or all of $R_1$ and $R_2$, $R_3$ and $R_4$, and $R_5$ and $R_6$ may be taken together to form an aryl group. For example, $R_1$ and $R_2$ may be taken together to form an aryl group; alternatively or in addition, $R_3$ and $R_4$ may be taken together to form an aryl group; alternatively or in addition, $R_5$ and $R_6$ may be taken together to form an aryl group. In certain preferred embodiments of the present invention, the aryl group formed by any of these pairs is selected from the group consisting of

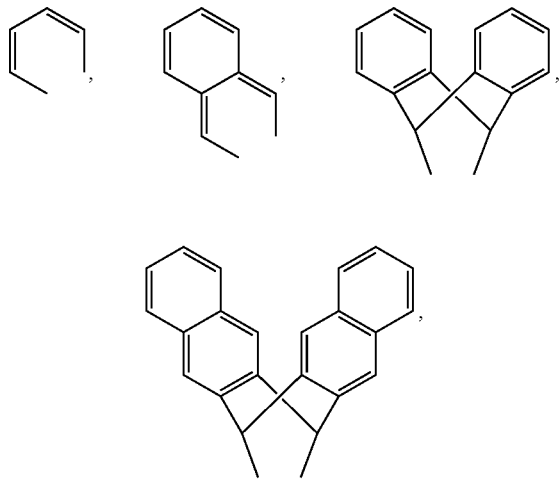

-continued

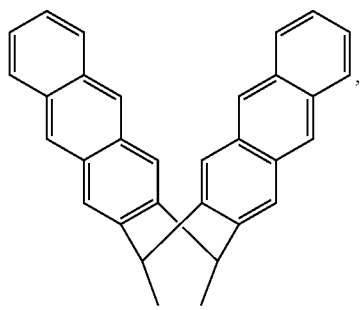

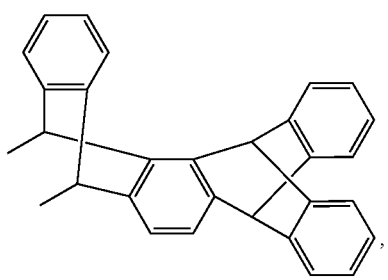

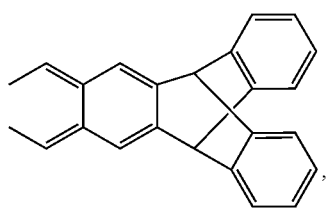

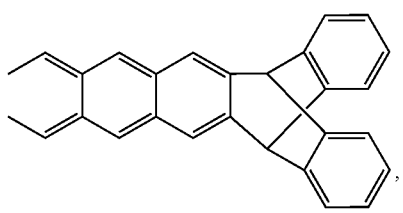

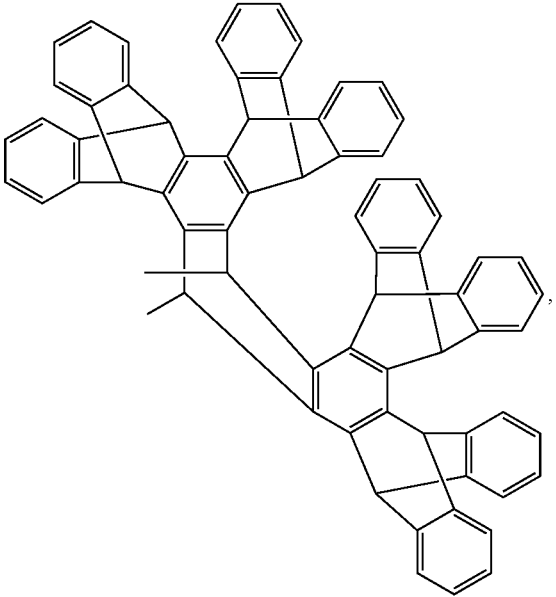

17
-continued

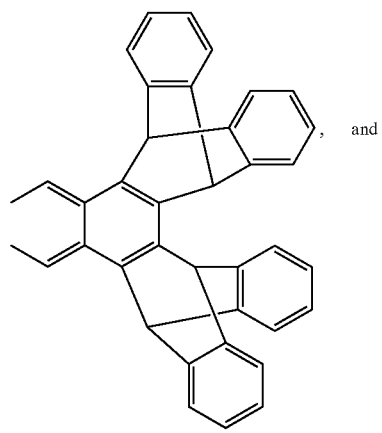, and

18
-continued

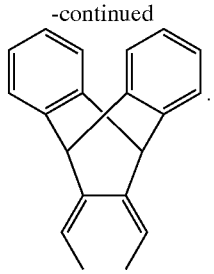.

Further, when present, any or all of $R_1$–$R_6$ may represent a charge-transport substituent. The presence of such a charge transport substituent can improve charge balance and enhance overall device performance. The charge transport substituent can be a hole transport group or an electron transport group. In preferred embodiments of the present invention, the charge transport substituent is selected from the group consisting of

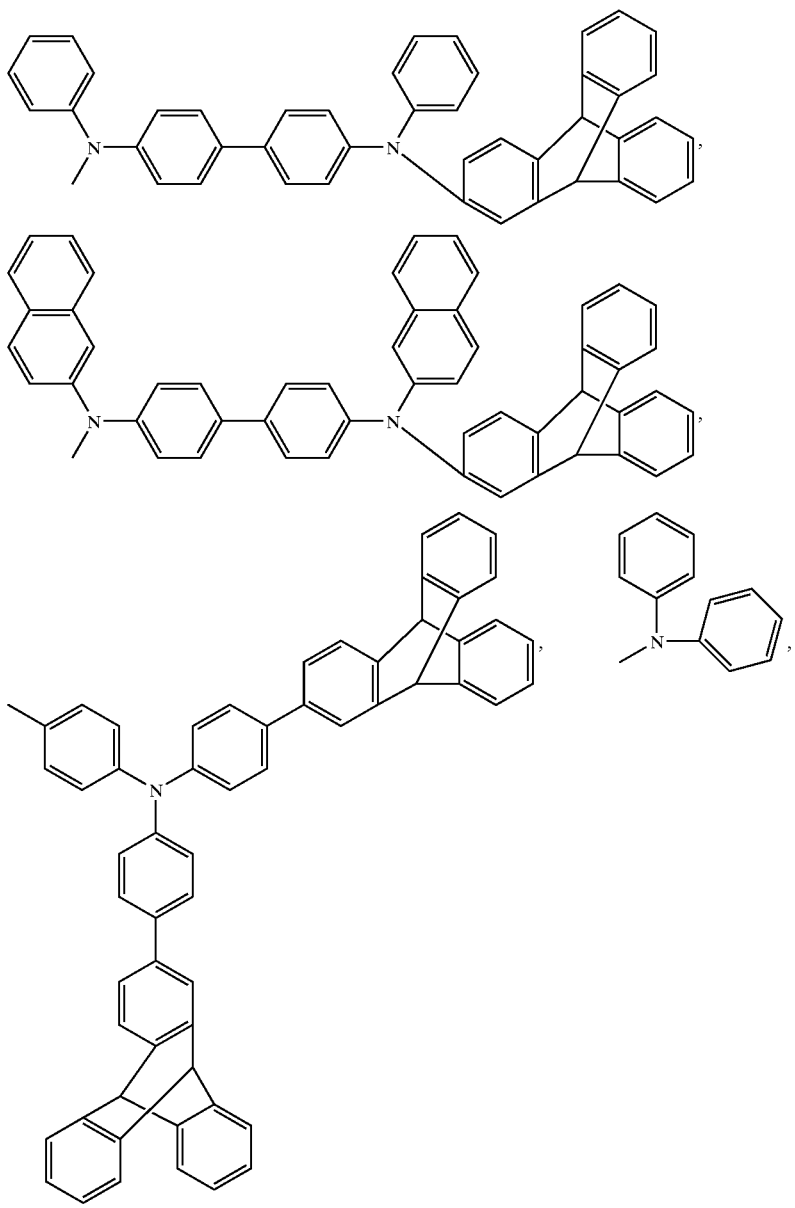

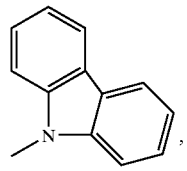
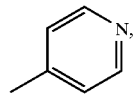, and
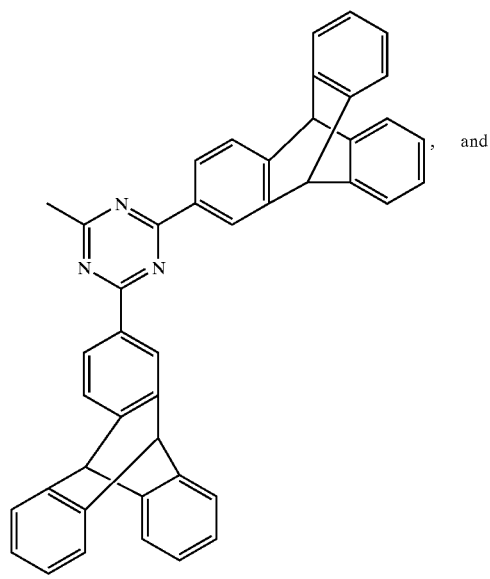
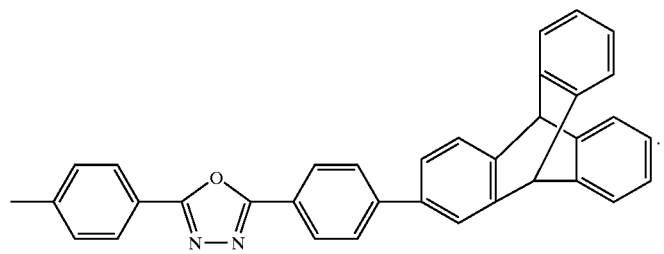
In preferred embodiments of the present invention, the iptycene derivative is selected from the group consisting of
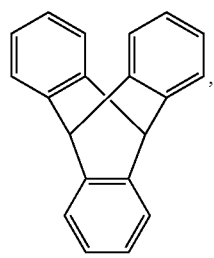
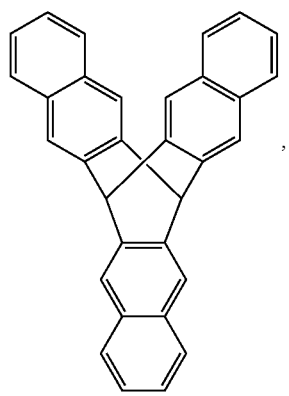,

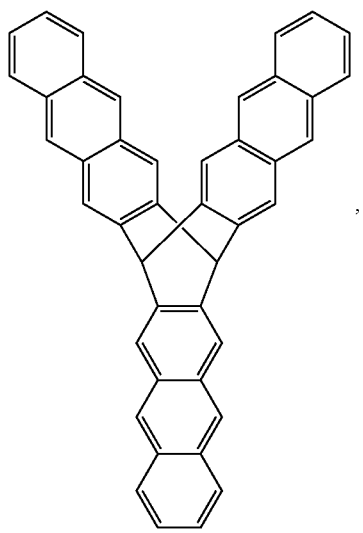
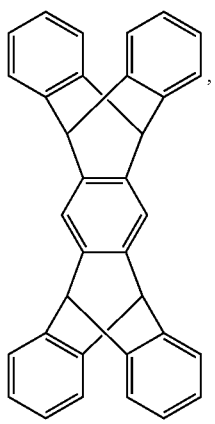
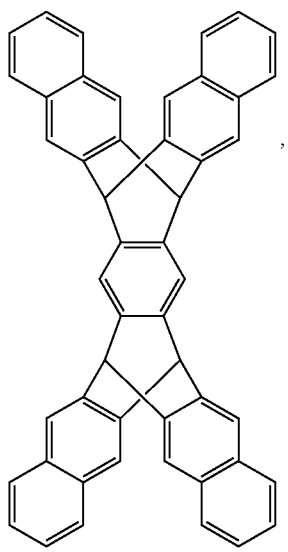
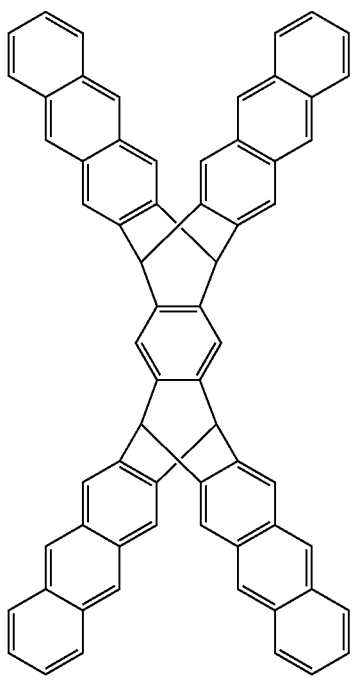
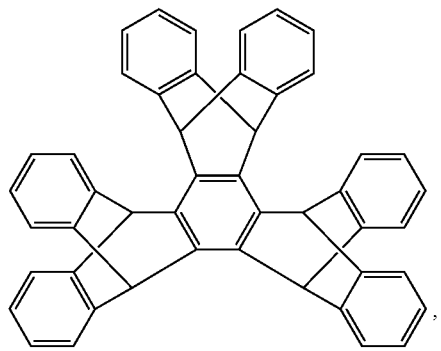
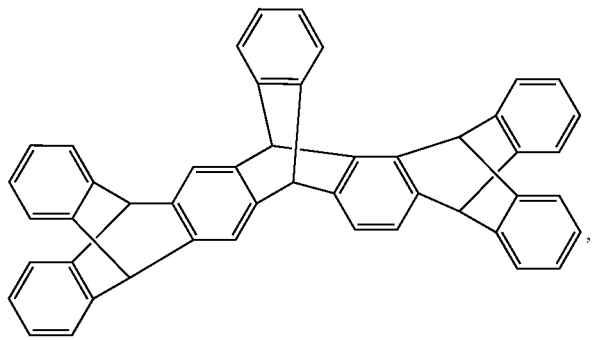

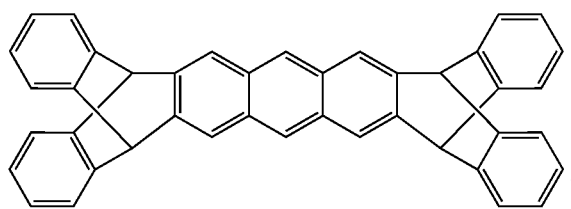
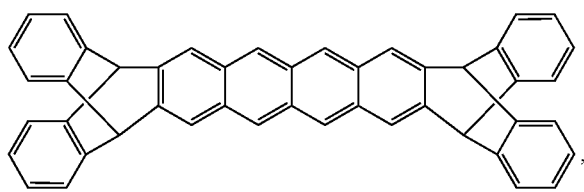
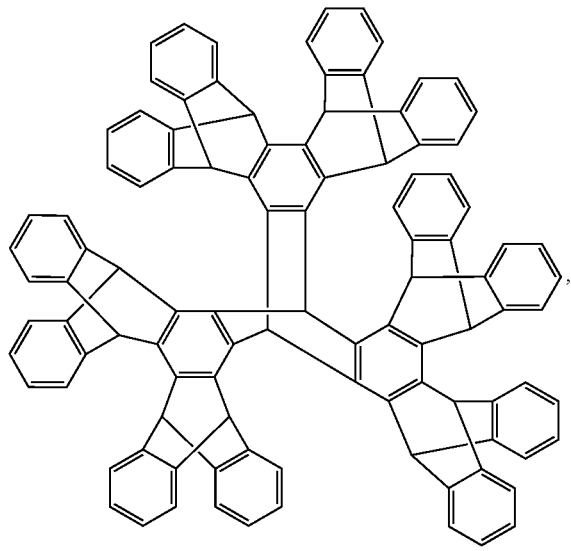
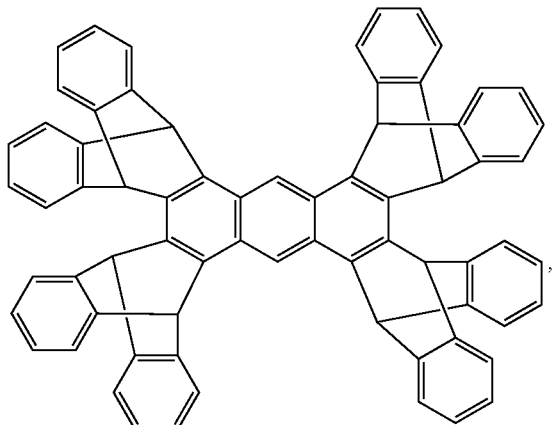
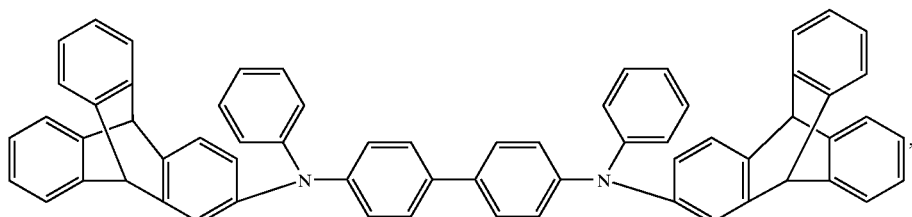
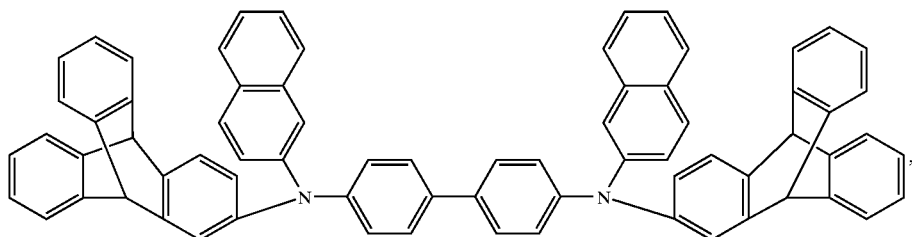
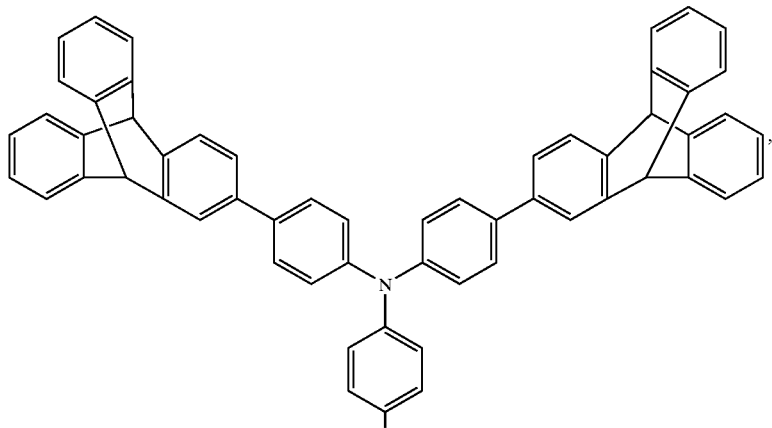

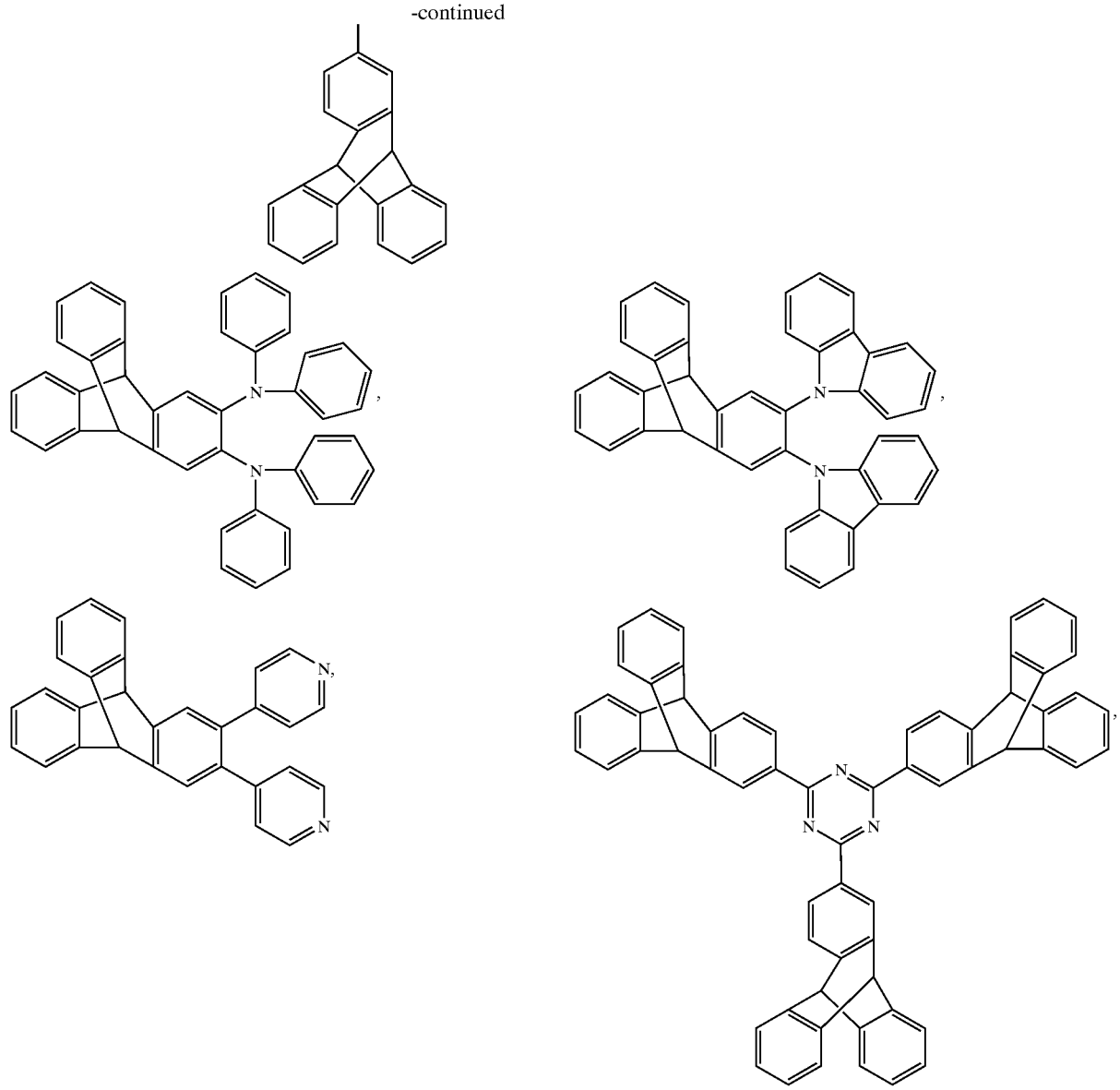

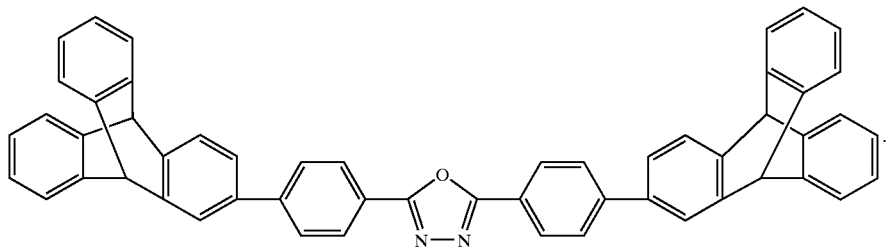

and

In this aspect of the invention, the above-described iptycene derivative can be used directly as the emissive layer or can be used as a host material for an emissive dopant in a case where the emissive layer comprises an iptycene host plus an emissive dopant. Any known emissive material can be used as the emissive dopant. One ordinarily skilled in the art would readily understand that the amount of host or dopant in a given emissive layer varies depending on the overall desired result. Typically, the dopant is present in an amount of 0.1–20% by weight.

A further aspect of the invention is directed to an OLED having an emissive layer sandwiched between at least one charge transport layer and an anode and a cathode. The charge transport layer can be either an electron transport layer or a hole transport layer, or both. According to this aspect of the invention, the charge transport layer includes an iptycene derivative according to the above general formula (I) wherein $R_1$ through $R_6$ are specified above.

In a preferred embodiment of this aspect of the invention, the iptycene derivative is substituted with a charge transport group in order to enhance performance of the iptycene derivative as a charge transport material or host material therefor. The charge transport group can be a hole transport group or an electron transport group. In preferred embodiments of the present invention, the charge transport substituent is selected from hole transport groups such as

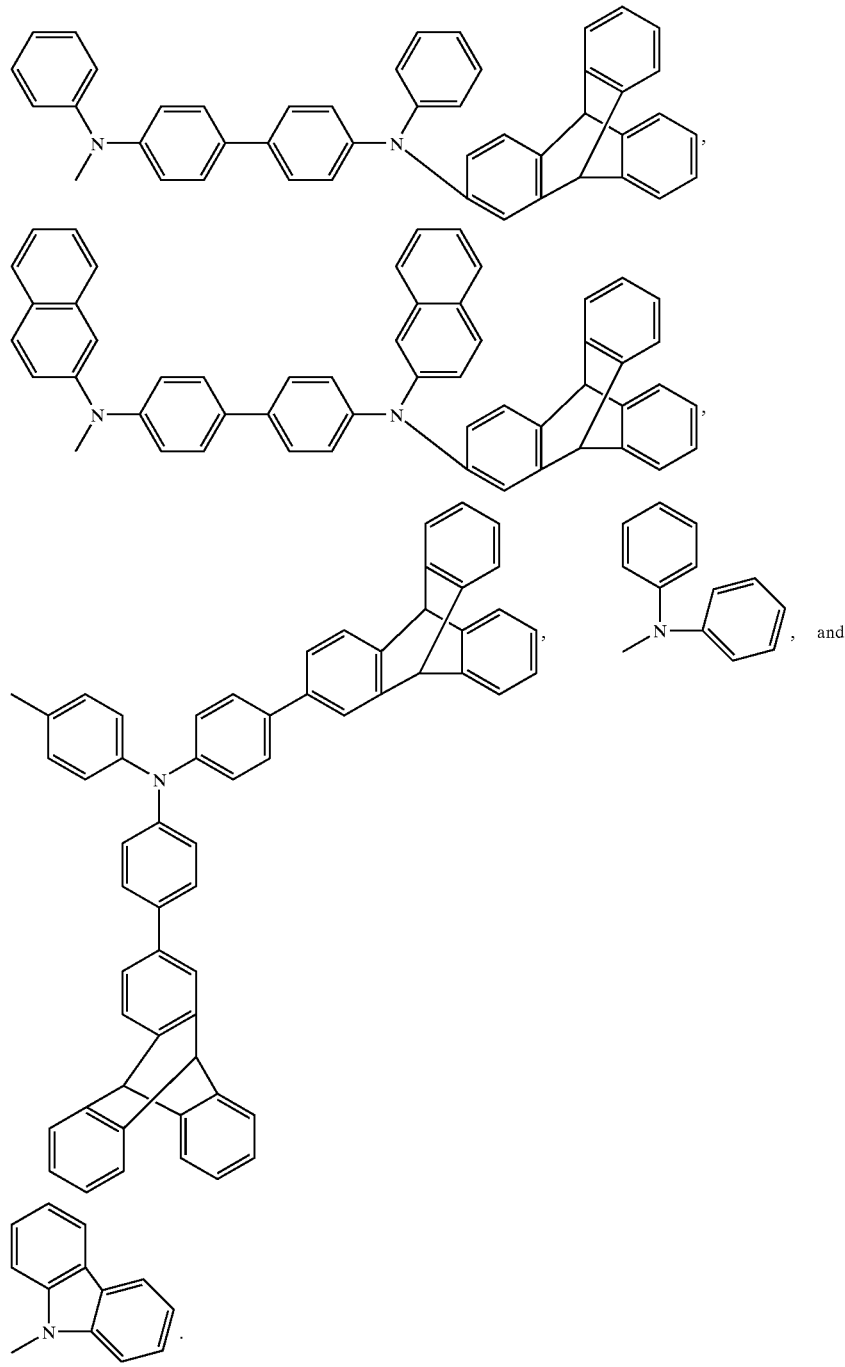

In other preferred embodiments, the charge transport group is selected from electron transport groups such as

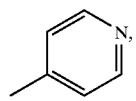

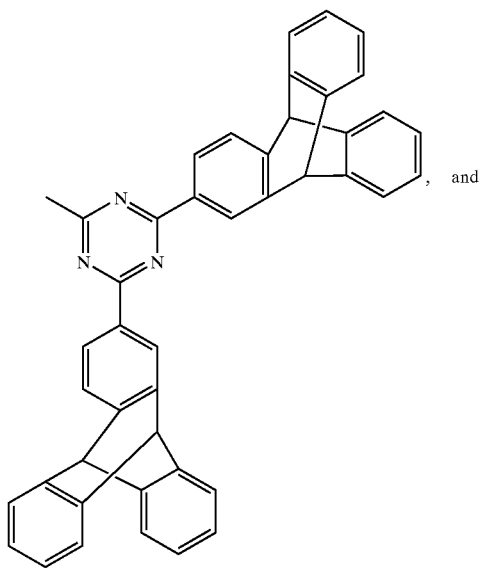
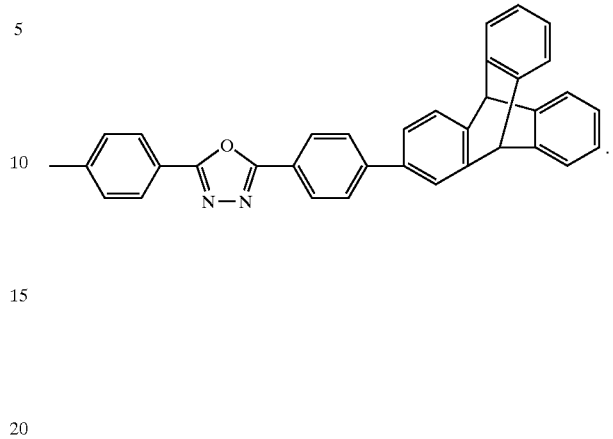
Iptycene derivatives substituted with hole transport groups suitable for use in the present invention include, without limitation:
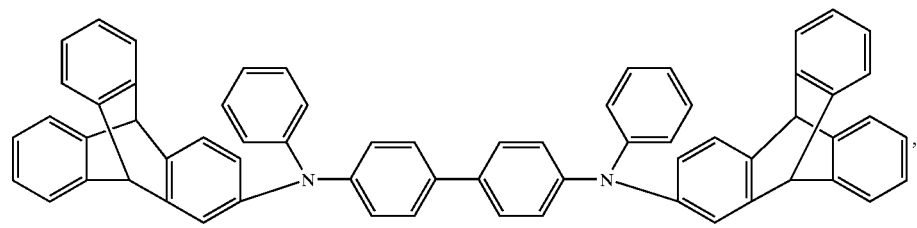
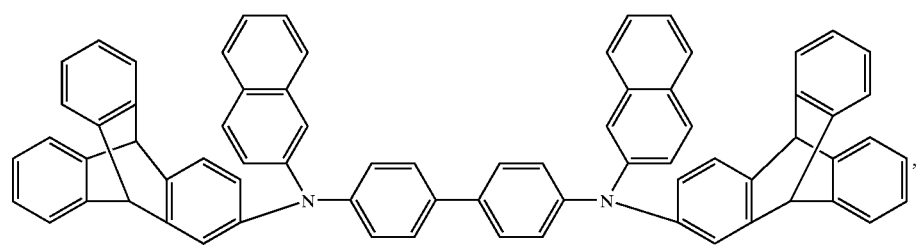
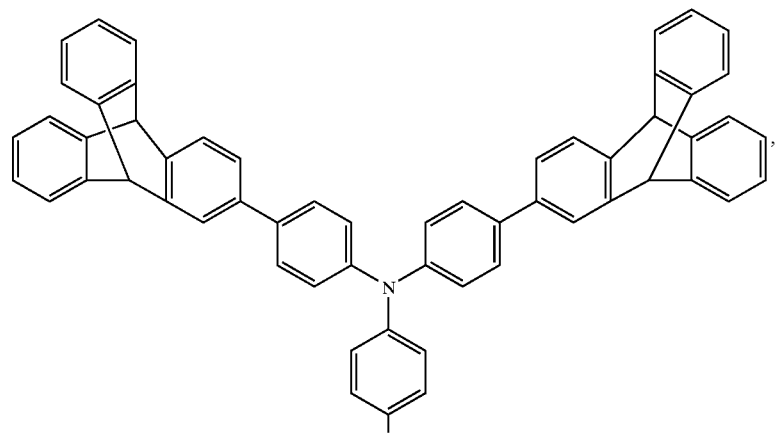

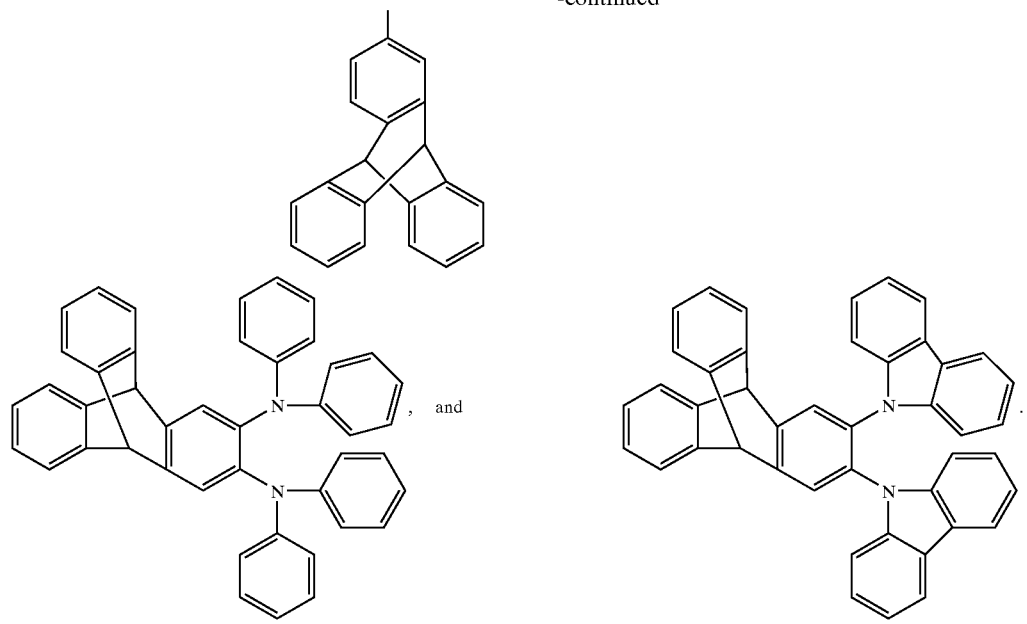
Iptycene derivatives substituted with electron transport groups suitable for use in the present invention include, without limitation:
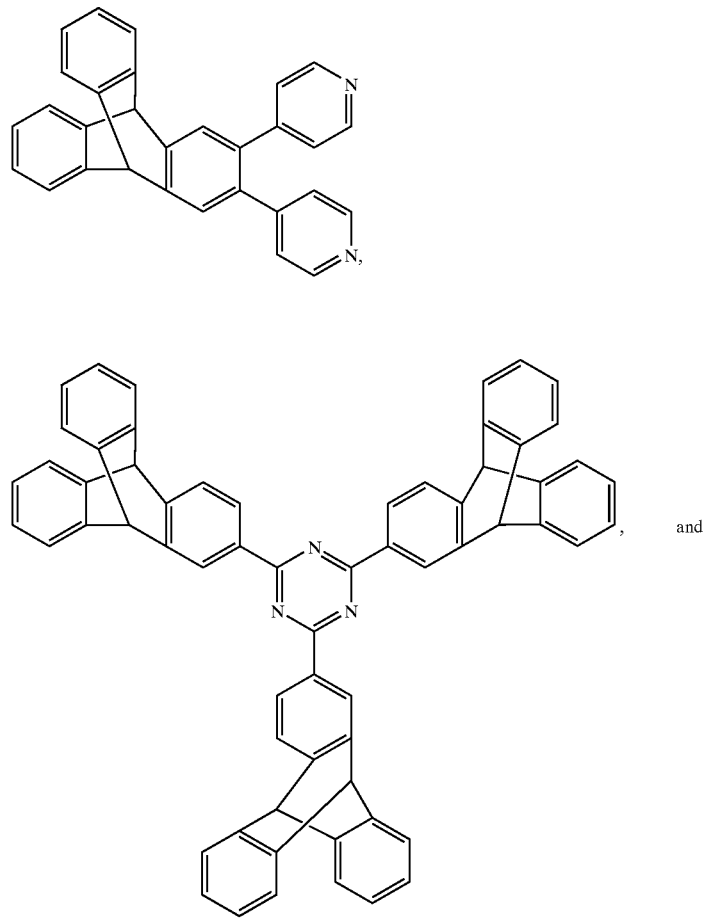

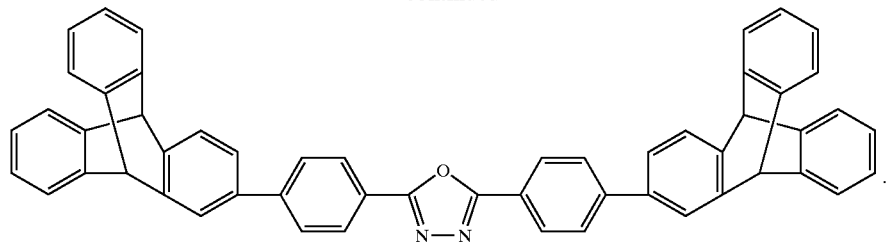

According to this aspect of the invention, the compound expressed according to formula (I) can be used directly as the charge transport layer or can form a charge transport host material in a case where the charge transport layer comprises a host material plus a charge transport dopant. Any known charge transport material can be used as the charge transport dopant. One ordinarily skilled in the art would readily understand that the amount of host or dopant in a given charge transport layer varies depending on the overall desired result. Typically, the dopant is present in an amount of 0.1–20% by weight.

The following specific examples of the synthesis of iptycene derivatives and of OLEDs incorporating such iptycene derivatives in accordance with the present invention are for illustration purposes and are not to be considered limiting of the invention, which is defined by the claims.

EXAMPLE 1

Synthesis of Compounds 1, 2, 3

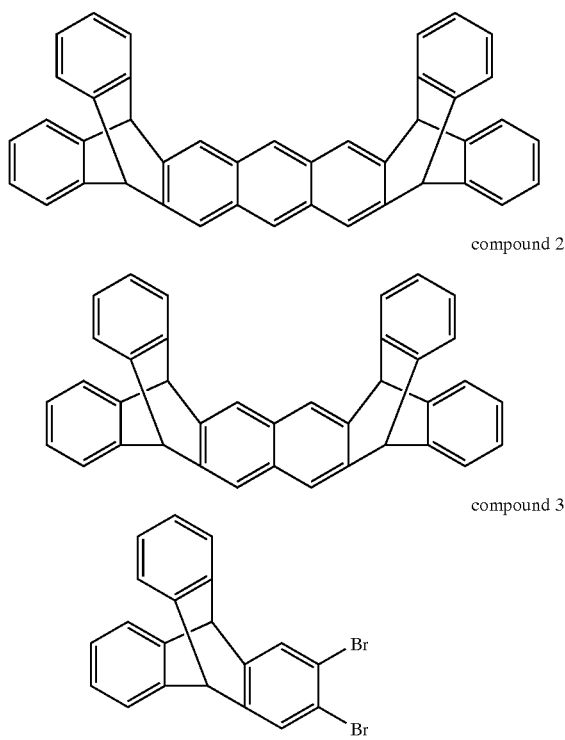

Compounds 1, 2, and 3 (dibromotriptycene) were synthesized according to known procedures (see Hart, et al., "Iptycenes: Extended Triptycenes", Tetrahedron, vol. 42, no. 6, p. 1641 (1986)).

EXAMPLE 2

Synthesis of Compound 4

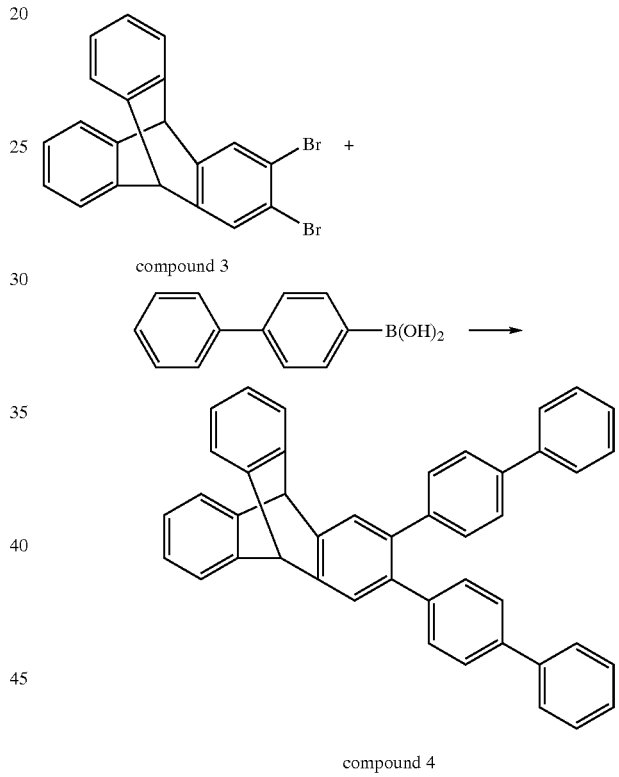

A round flask was charged with compound 3 (0.824 g, 2 mmol), 4-biphenylboronic acid (1.2 g, 6 mmol), Pd(0)(PPh$_3$)$_4$ (120 mg), and a mixture of 20 mL of dry toluene and 10 mL of dry ethanol. After stirring for 10 min at room temperature, a 10 mL solution of degassed 2M of aqueous Na$_2$CO$_3$ was added to the reaction solution. The reaction mixtures were stirred at 80° C. under N$_2$ for two days. After cooling down, the mixture was poured into water. The product was extracted with toluene, washed with water, dried over MgSO$_4$. After filtration and concentration, it was purified through column chromatography (silica gel, mixtures of CH$_2$Cl$_2$/hexanes). Yield: 75%. It had a Td at 310° C. by TGA.

EXAMPLE 3

Synthesis of Compound 5

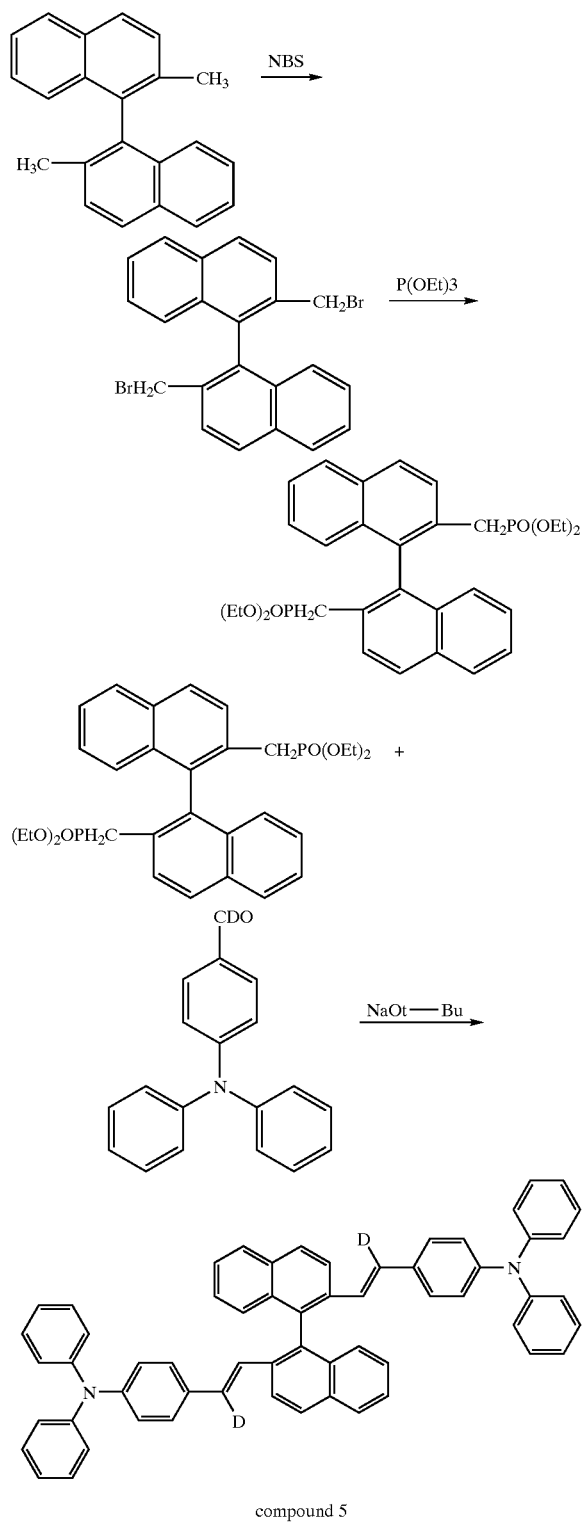

compound 5

Compound 5 was synthesized via a few step reactions. 2,2'-dibromomethyl-1,1'-binaphthyl was obtained by reaction of N-bromosuccinimide (NBS) with 2,2'-dimethyl-1,1'-binaphthyl according to a known reference procedure (see Maigrot et al., Synthesis, pp. 317–320 (1985)). Refluxing of 2,2'-dibromomethyl-1,1'-binaphthyl in an excess of triethylphosphite afforded the ester compound. The deuterated 4-aldehydetriphenylamine was obtained by a reaction of triphenylamine (1 equiv.) and deuterated dimethylformamide-d7 (DMF-d7) (1.4 equiv.) in the presence of POCl$_3$ (1.2 equiv.) according to a similar reference procedure (see Li, et al., Chem. Mater., vol. 11, pp. 1568–1575(1999)). Finally, a round flask was charged with 1,1'-binaphthyl ester compound (0.77 g, 1.39 mmol), deuterated 4-aldehydetriphenylamine (0.8 g, 2.92 mmol), NaOt-Bu (0.4 g, 4.17 mmol), and 10 mL of dry DMF. The mixture was stirred at room temperature under N$_2$ for two days. The mixture was poured into 100 mL of water. The precipitate was filtered and washed with water and methanol. It was purified through column chromatography (silica gel, mixtures of CH$_2$Cl$_2$/hexanes). Yield: 50%. It had a Tg at 122° C. by DSC. This compound shows a good blue emission.

EXAMPLE 4

Synthesis of Compound 6

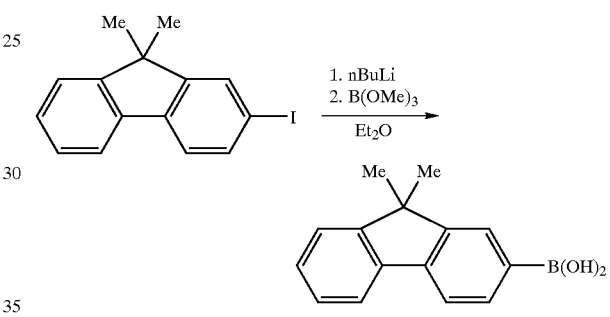

15% n-Butyllithium n-hexane solution (35.6 ml, 55 mmol) was added to a solution of 2-iododimethylfluorene (16 g, 50 mmol) dissolved in 170 ml of diethylether on a dry ice-acetone bath at −78° C. under nitrogen. After stirring the slurry solution for 2.5 h, the reaction mixture was allowed to warm to room temperature, followed by stirring for 1 h. The solution was again cooled on the bath at −78° C. Trimethylborate (27.4 ml, 0.240 mmol) was then added to the solution. The solution was stirred at the low temperature for 1 h and at room temperature for 1 h. The resulting reaction mixture was stand alone at room temperature over night. Half of the solvent was evaporated, followed by adding 50 ml of water and continuously 140 ml of 2M HCl aqueous solution. The precipitate was filtrated and washed with toluene. The solvent was removed from the organic phase, giving the additional boronic acid. The solid was also washed with toluene. The product was dried in vacuo. White solid, Yield: 70%.

EXAMPLE 5

Synthesis of Compound 7

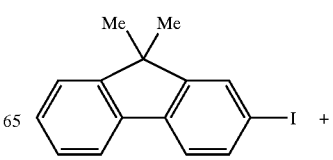

-continued

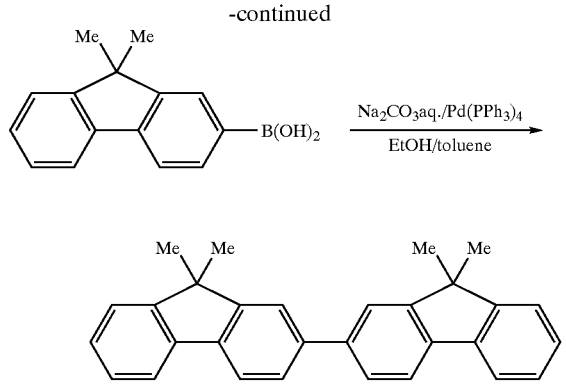

2-Iododimethylfluorene (1.98 g, 6.18 mmol) and 1.5 g (4.73 mmol) of dimethylfluorene-2-boronic acid were dissolved in a mixture of degassed toluene (80 ml) and degassed ethanol (40 ml). Sodium carbonate aqueous solution (41 ml), which was prepared by dissolving 9 g of sodium carbonate in 45 ml of water, was added to the solution, followed by stirring at room temperature for 30 min. To the resulting hazy solution was added 238 mg (0.206 mmol) of Pd(PPh$_3$)$_4$ as a solid. The solution was then heated on an oil bath at 80° C. for 5 h under nitrogen flow. After cooling to room temperature, ethyl acetate and water were added to the reaction mixture. The organic phase and the water phase were separated. The water phase was extracted with toluene and ethyl acetate. The combined organic phase was dried over MgSO$_4$ and the solvents were evaporated. The desirable product was isolated by a silica-gel column chromatography eluted by a 2:1 (or 3:1) mixture of n-hexane and toluene. If the product was not so pure, further purification using the silica-gel column would be desirable. White pale yellow solid, Yield: 90%.

EXAMPLE 6

Synthesis of Compound 8

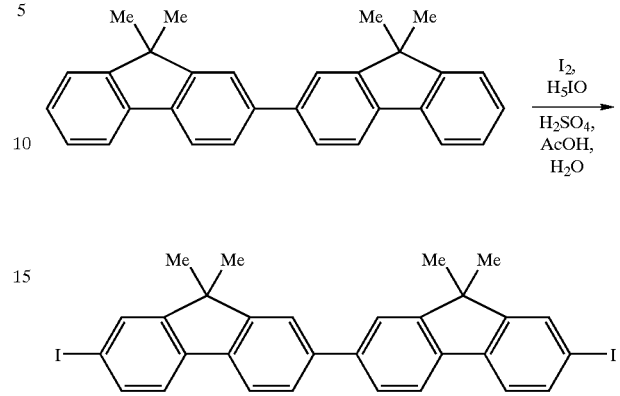

To compound 7 (350 mg, 0.907 mmol), 164 mg (0.72 mmol) of H$_5$I$_6$O$_6$—H$_2$O, and 366 mg of I2 (2.88 mmol) in 20 ml of acetic acid was added a mixture of H$_2$SO$_4$ (6 ml) and H$_2$O (4 ml). The solution was stirred at 80° C. for 3 h, giving a pale red solution. After cooling the solution to room temperature, water was added. The solid thus precipitated was filtrated, followed by washing the precipitate with water and n-hexane. The product was dried in vacuo. Pale red solid (when purified by a silica gel column, the pale red color disappeared), Yield: 80%.

EXAMPLE 7

Synthesis of Compound 9

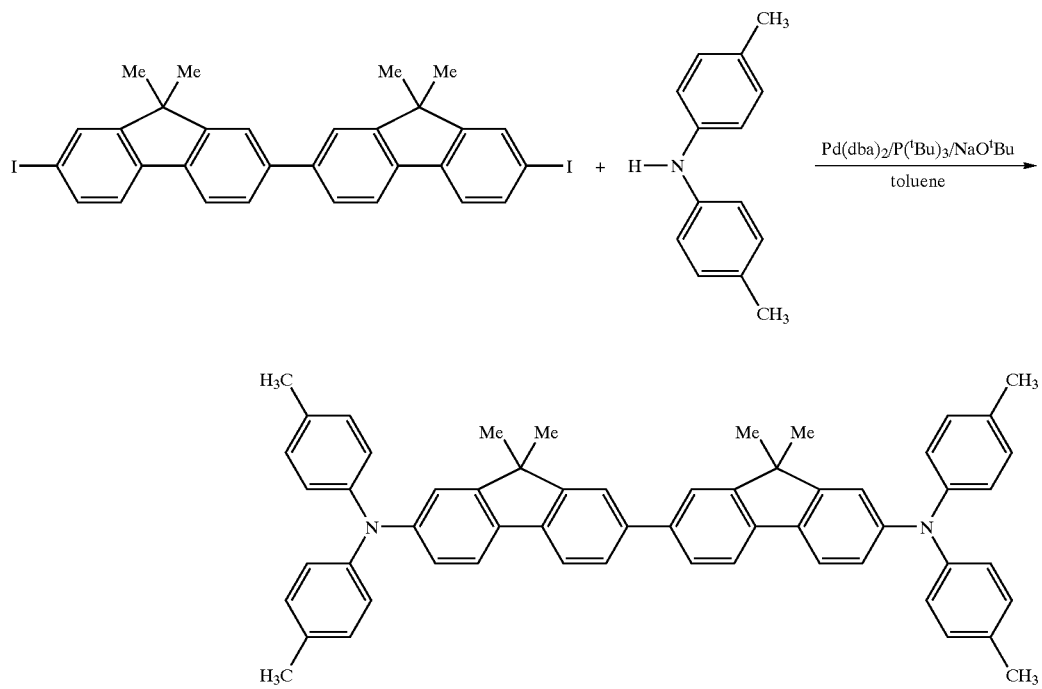

To a solution of Pd(dba)$_2$ (72 mg, 0.125 mmol) in 10 ml of toluene was added 76 mg of tris(tert-butyl)phosphine in 3 ml of toluene, followed by stirring for 30 min under nitrogen. 2,7-Diiododimethylfluorene (360 mg, 0.564 mmol) dissolved in 20 ml of toluene was added to the dark-brown catalyst solution. After stirring the solution for about 20 min, 217 mg (2.26 mmol) of sodium tert-butoxide was added as a solid. The solution was heated on an oil-bath at 80° C. for 5 h. The reaction mixture was quenched with water. The water phase was extracted with toluene and ethyl acetate. The organic phase was dried over MgSO$_4$ and then the solvents were evaporated. The product was isolated by a silica gel column chromatography eluted by a 2:1 (or 3:1) mixture of n-hexane and toluene. If the product was not so pure, further purification using the silica gel column or recrystallization would be desirable. Pale yellow solid, Yield: 70%.

EXAMPLE 8

ITO/NPD/Compound 1/Bphen/Li—Al/Al OLED

An OLED was manufactured using compound 1 as an emissive material, NPD as a hole transporter, Bphen as an electron transporter, Li—Al alloy as an electron injection material and ITO and Al as electrode materials according to the method set forth below:

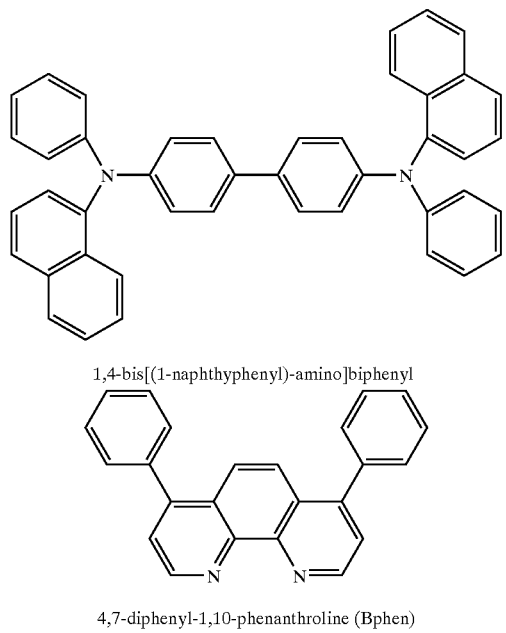

1,4-bis[(1-naphthyphenyl)-amino]biphenyl 4,7-diphenyl-1,10-phenanthroline (Bphen)

A clean substrate coated with a patterned layer with an area of 0.0314 cm$^2$ of ITO was obtained. The substrate was treated with O$_2$ plasma for 1–5 minutes. Then, the substrate was placed in a thermal evaporator, and the pressure was pumped down below 6×10$^{-6}$ torr. Next, a 20 nm NPD hole transport layer was evaporated onto the substrate. Then, a 20 nm emissive layer consisting of Compound 1 was evaporated thereon. Then, a 40 nm Bphen electron transport layer was evaporated at a rate of approximately 1–3 Å/s thereon. Next, a mask was placed next to the substrate to define where the metal is to be evaporated. Then, a 12 nm Li—Al (1:9) alloy was evaporated to improve electron injection into the device. Finally, a 150 nm Al electrode was deposited, and the evaporator was allowed to cool. Evaporation was accomplished using an ULVAC VPC-1100 (Sinku Kiko).

The device obtained by the above process was tested for luminance, color, and current-voltage characteristics. A driving voltage was applied to the obtained device by connecting the ITO electrode to a positive electrode(+) and the Al cathode to a negative electrode(−) to test emission of light, and a uniform light of blue color was obtained. The following device data were obtained: the density of electric current: 300 mA/cm$^2$ at 8 V, the luminance: 1380 cd/m$^2$ at 8 V, and the maximum external quantum efficiency: 0.4%, the maximum external power efficiency 0.45 lm/W, CIE color coordinates were (0.18, 0.15).

EXAMPLE 9

ITO/NPD/Compound 1+Compound 5/Bphen/Li—Al/Al OLED

An OLED was manufactured using compound 1 as host material for compound 5 as an emissive material, NPD as a hole transporter, Bphen as an electron transporter, Li—Al alloy as an electron injection material and ITO and Al as electrode materials according to the method set forth below:

A clean substrate coated with a patterned layer with an area of 0.0314 cm$^2$ of ITO was obtained. The substrate was treated with O$_2$ plasma for 1–5 minutes. Then, the substrate was placed in a thermal evaporator, and the pressure was pumped down below 6×10$^{-6}$ torr. Next, a 20 nm NPD hole transport layer was evaporated onto the substrate. Then, a 30 nm emissive layer consisting of compound 1 and 1% wt. compound 5 was formed thereon. With the shutter of the deposition chamber closed to prevent premature deposition, evaporation of the dopant (compound 5) was stabilized at a rate around 0.03 Å/s, then the evaporation of the host (compound 1) was stabilized at a rate around 1–3 Å/s, giving a doping concentration of about 1–3%. The shutter was then opened, and the deposition was monitored by a quartz crystal monitor. Then, a 30 nm Bphen electron transport layer was evaporated at a rate of approximately 1–3 Å/s thereon. Next, a mask was placed next to the substrate to define where the metal is to be evaporated. Then, a 12 nm Li—Al (1:9) alloy was evaporated to improve electron injection into the device. Finally, a 150 nm Al electrode was deposited, and the evaporator was allowed to cool.

The driving voltage was applied to the obtained device by connecting the ITO electrode to a positive electrode(+) and the cathode of Al to a negative electrode(−) to test emission of light, and a uniform light of blue color was obtained. The following device data were obtained: the density of electric current: 30 mA/cm$^2$ at 8 V, the luminance: 600 cd/m$^2$ at 8 V, and the maximum external quantum efficiency: 1.4%, the maximum external power efficiency 1.2 lm/W, CIE color coordinates were (0.15, 0.20).

EXAMPLE 10

ITO/NPD/Compound 1+1% wt. Compound 9/Bphen/Li—Al/Al OLED

An OLED was manufactured using compound 1 as host material for compound 9 as a blue emissive material, NPD as a hole transporter, Bphen as an electron transporter, Li—Al alloy as an electron injection material and ITO and Al as electrode materials according to the method set forth below:

A clean substrate coated with a patterned layer with an area of 0.0314 cm$^2$ of ITO was obtained. The substrate was treated with O$_2$ plasma for 1–5 minutes. Then, the substrate was placed in a thermal evaporator, and the pressure was pumped down below 6×10⁻⁶ torr. Next, a 20 nm NPD hole transport layer was evaporated onto the substrate. Then, a 30 nm emissive layer consisting of compound 1 and 1% wt. compound 9 was formed thereon. With the shutter of the deposition chamber closed to prevent premature deposition, evaporation of the dopant (compound 9) was stabilized at a rate around 0.03 Å/s, then the evaporation of the host (compound 1) was stabilized at a rate around 1–3 Å/s, giving a doping concentration of about 1–3%. The shutter was then opened, and the deposition was monitored by a quartz crystal monitor. Then, a 30 nm Bphen electron transport layer was evaporated at a rate of approximately 1–3 Å/s thereon. Next, a mask was placed next to the substrate to define where the metal is to be evaporated. Then, a 12 nm Li—Al (1:9) alloy was evaporated to improve electron injection into the device. Finally, a 150 nm Al electrode was deposited, and the evaporator was allowed to cool.

The driving voltage was applied to the obtained device by connecting the ITO electrode to a positive electrode(+) and the cathode of Al to a negative electrode(−) to test emission of light, and a uniform light of blue color was obtained. The following device data were obtained: the density of electric current: 40 mA/cm² at 8 V, the luminance: 400 cd/m² at 8 V, and the maximum external quantum efficiency: 1.2%, the maximum external power efficiency 0.6 lm/W, CIE color coordinates were (0.17, 0.14).

EXAMPLE 11

ITO/NPD/Compound 1+2% wt. Compound 9/ Bphen/Li—Al/Al OLED

An OLED was manufactured using compound 1 as host material for compound 9 as a blue emissive material, NPD as a hole transporter, Bphen as an electron transporter, Li—Al alloy as an electron injection material and ITO and Al as electrode materials according to the method set forth below:

A clean substrate coated with a patterned layer with an area of 0.0314 cm² of ITO was obtained. The substrate was treated with O₂ plasma for 1–5 minutes. Then, the substrate was placed in a thermal evaporator, and the pressure was pumped down below 6×10⁻⁶ torr. Next, a 20 nm NPD hole transport layer was evaporated onto the substrate. Then, a 30 nm emissive layer consisting of compound 1 and 2% wt. compound 9 was formed thereon. With the shutter of the deposition chamber closed to prevent premature deposition, evaporation of the dopant (compound 9) was stabilized at a rate around 0.03 Å/s, then the evaporation of the host (compound 1) was stabilized at a rate around 1–3 Å/s, giving a doping concentration of about 1–3%. The shutter was then opened, and the deposition was monitored by a quartz crystal monitor. Then, a 30 nm Bphen electron transport layer was evaporated at a rate of approximately 1–3 Å/s thereon. Next, a mask was placed next to the substrate to define where the metal is to be evaporated. Then, a 12 nm Li—Al (1:9) alloy was evaporated to improve electron injection into the device. Finally, a 150 nm Al electrode was deposited, and the evaporator was allowed to cool.

The driving voltage was applied to the obtained device by connecting the ITO electrode to a positive electrode(+) and the cathode of Al to a negative electrode(−) to test emission of light, and a uniform light of blue color was obtained. The following device data were obtained: the density of electric current: 60 mA/cm² at 6 V, the luminance: 750 cd/m² at 6 V, and the maximum external quantum efficiency: 1.7%, the maximum external power efficiency 1.4 lm/W, CIE color coordinates were (0.16, 0.13).

EXAMPLE 12

ITO/NPD/Compound 2+2% wt. Compound 9/ Bphen/Li—Al/Al OLED

An OLED was manufactured using compound 2 as host material for compound 9 as a blue emissive material, NPD as a hole transporter, Bphen as an electron transporter, Li—Al alloy as an electron injection material and ITO and Al as electrode materials according to the method set forth below:

A clean substrate coated with a patterned layer with an area of 0.0314 cm² of ITO was obtained. The substrate was treated with O₂ plasma for 1–5 minutes. Then, the substrate was placed in a thermal evaporator, and the pressure was pumped down below 6×10⁻⁶ torr. Next, a 20 nm NPD hole transport layer was evaporated onto the substrate. Then, a 30 nm emissive layer consisting of compound 2 and 2% wt. compound 9 was formed thereon. With the shutter of the deposition chamber closed to prevent premature deposition, evaporation of the dopant (compound 9) was stabilized at a rate around 0.03 Å/s, then the evaporation of the host (compound 1) was stabilized at a rate around 1–3 Å/s, giving a doping concentration of about 1–3%. The shutter was then opened, and the deposition was monitored by a quartz crystal monitor. Then, a 30 nm Bphen electron transport layer was evaporated at a rate of approximately 1–3 Å/s thereon. Next, a mask was placed next to the substrate to define where the metal is to be evaporated. Then, a 12 nm Li—Al (1:9) alloy was evaporated to improve electron injection into the device. Finally, a 150 nm Al electrode was deposited, and the evaporator was allowed to cool.

The driving voltage was applied to the obtained device by connecting the ITO electrode to a positive electrode(+) and the cathode of Al to a negative electrode(−) to test emission of light, and a uniform light of blue color was obtained. The following device data were obtained: the density of electric current: 40 mA/cm² at 6 V, the luminance: 300 cd/m² at 6 V, and the maximum external quantum efficiency: 1.2%, the maximum external power efficiency 0.9 lm/W, CIE color coordinates were (0.18, 0.15).

The preceding examples are provided to illustrate the invention, and are not to be considered limiting of the invention, which is defined by the following claims.

What is claimed is:

1. An organic light emitting device comprising:
   an emissive layer sandwiched between at least a cathode and an anode,
   wherein the organic layer comprises an iptycene derivative having the formula:

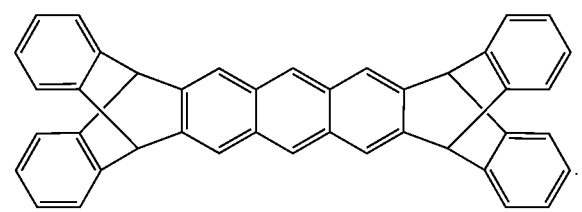

2. The organic light emitting device according to claim 1, wherein the emissive layer comprises only the iptycene derivative.

3. The organic light emitting device according to claim 1, wherein the emissive layer comprises an emissive material and the iptycene derivative as a host material.

* * * * *